United States Patent [19]

Remers

[11] Patent Number: 4,617,389
[45] Date of Patent: * Oct. 14, 1986

[54] MITOMYCIN ANALOGS
[75] Inventor: William A. Remers, Tucson, Ariz.
[73] Assignee: University Patents, Inc., Westport, Conn.
[*] Notice: The portion of the term of this patent subsequent to May 19, 1998 has been disclaimed.
[21] Appl. No.: 561,787
[22] Filed: Dec. 15, 1983

Related U.S. Application Data

[63] Continuation of Ser. No. 264,187, May 15, 1981, abandoned.
[51] Int. Cl.$^4$ .................... C07D 487/04; A61K 31/40
[52] U.S. Cl. .................... 544/142; 544/372; 544/60; 546/143; 546/161; 546/133; 546/153; 546/271; 548/126; 548/127; 548/128; 548/134; 548/138; 548/181; 548/222; 548/255; 548/266; 548/371; 548/372; 548/374; 548/422
[58] Field of Search ............... 424/274; 548/422, 181, 548/138, 131, 127, 128, 126, 374, 371, 372, 266, 255; 546/133, 143, 153, 161, 271; 544/60, 142, 372

[56] References Cited

U.S. PATENT DOCUMENTS 3,332,944  7/1967  Cosulich et al. ............ 424/274
3,410,862  11/1968 Matsui et al. .............. 424/274
3,429,894  2/1969  Matsui et al. .............. 424/274
4,268,676  5/1981  Remers ................... 548/522 X
4,460,599  7/1984  Remers ................... 548/522 X

OTHER PUBLICATIONS

Burger, ed., *Medicinal Chemistry*, 3rd ed., Wiley–Interscience (1970), pp. 65, 67, 71, 75.
*Merk Index*, 9th ed., Merk and Co., 1976, pp. 807–808, Abstract #6060.
Burger, ed., *Medicinal Chemistry*, Third ed., Wiley–Interscience, N.Y., (1970) pp. 72–74.

*Primary Examiner*—Donald G. Daus
*Assistant Examiner*—William A. Teoli, Jr.
*Attorney, Agent, or Firm*—Marshall, O'Toole, Gerstein, Murray & Bicknell

[57] ABSTRACT

Antineoplastic compounds of the formula, IIa,

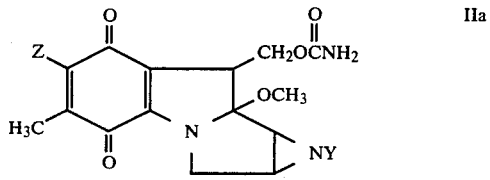

wherein:
Y is hydrogen or lower alkyl; and Z is a lower alkoxy substituted quinolinylamino radical, a cyano substituted pyrazolylamino radical or a mono- or di-lower alkyl substituted thiazolamino radical, or a nitrogen-containing heterocyclic radical, or a cyano, phenyl, carboxamido or lower alkoxycarbonyl substituted 1-aziridinyl radical or a lower alkyl, formyl or acetylphenyl substituted 1-piperazinyl radical, or an hydroxy or piperidyl substituted 1-piperidyl radical, or a lower alkoxy, amino or halo substituted pyridylamino radical, or a carboxamido, mercapto or methylenedioxy substituted anilino radical, or a radical of the formula,

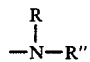

wherein
R is hydrogen or lower alkyl and R" is a nitrogen-containing heterocyclic radical, or
a butyrolactonyl radical, or
an adamantyl radical, or
a mono- lower alkoxy substituted phenyl radical, or
a substituted lower alkyl radical selected from the group consisting of mercapto lower alkyl, carboxy lower alkyl, mono-, di- and tri-lower alkoxy lower alkyl, lower alkyl thio lower alkyl and lower alkoxycarbonyl substituted derivatives thereof, cyano lower alkyl, mono-, di- and tri-lower alkoxy phenyl lower alkyl, phenyl cyclo lower alkyl, 1-pyrrolidinyl lower alkyl, N-lower alkyl pyrrolidinyl lower alkyl, N-morpholinyl lower alkyl, and lower dialkylamino lower alkyl.

10 Claims, No Drawings

MITOMYCIN ANALOGS

This is a continuation of application Ser. No. 264,187 filed May 15, 1981, now abandoned.

BACKGROUND

The present invention relates generally to antibiotic mitosane compounds and to their use in the treatment of neoplastic disease states in animals.

The disclosure of my allowed, co-pending U.S. patent application Ser. No. 100,331 (issued May 19, 1981 as U.S. Pat. No. 4,268,676) and my co-pending divisional U.S. patent application Ser. No. 206,529 thereon, filed Nov. 13, 1980 is specifically incorporated by reference herein for the purpose of providing both essential and nonessential material relating to the present invention.

Briefly summarized, said prior allowed application sets forth a staement of the background of the ongoing search in the art for new and useful compounds which are structurally related to the mitomycins, which possess antibiotic activity, which have low toxicity and which display a substantial degree of antitumor activity in animals. More particularly, said application discloses new compounds of the formula, I,

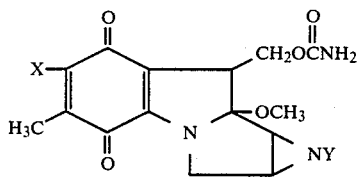

wherein: Y is hydrogen or lower alkyl; and X is a thiazolamino radical, a furfurylamino radical or a radical of the formula,

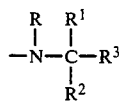

in which R, $R^1$ and $R^2$ are the same or different and selected from the group consisting of hydrogen and lower alkyl, and $R^3$ is selected from the group consisting of lower alkenyl, halo-lower alkenyl, lower alkynyl, lower alkoxycarbonyl, thienyl, formamyl, tetrahydrofuryl and benzene sulfonamide.

Said application also discloses novel methods for treatment of neoplastic disease states in animals, which methods comprise administering a therapeutically effective amount of a compound of the formula, Ia,

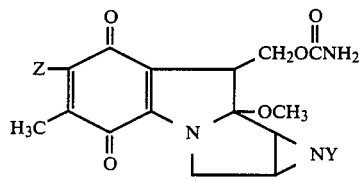

wherein: Y is hydrogen or lower alkyl; and Z is thiazolamino radical, a furfurylamino radical, a cyclopropylamino radical, a pryidylamino radical, or a radical of the formula,

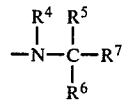

in which $R^4$, $R^5$, and $R^6$ are the same or different and selected from the group consisting of hydrogen and lower alkyl, and $R^7$ is selected from the group consisting of lower alkenyl, halo-lower alkenyl, lower alkynyl, lower alkoxycarbonyl, halo-lower alkyl, hydroxy-lower alkyl, pyridyl, thienyl, formamyl, tetrahydrofuryl, benzyl, and benzene sulfonamide.

BRIEF SUMMARY

According to the present invention, there are provided novel compounds of the formula, II,

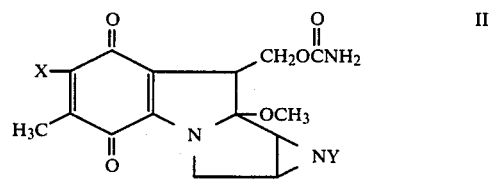

wherein:
Y is hydrogen or lower alkyl; and X is a lower alkoxy substituted quinolinylamino radical, a cyano substituted pyrazolylamino radical, or a mono- or di- lower alkyl substituted thiazolamino radical, or a nitrogen-containing heterocyclic radical selected from the group consisting of 1-pyrrolinyl, 1-indolinyl, N-thiazolidinyl and N-thiomorpholinyl radicals, or a cyano, phenyl, carboxamido or lower alkoxycarbonyl substituted 1-aziridinyl radical, or a lower alkyl, formyl or acetylphenyl substituted 1-piperazinyl radical, or an hydroxy or piperidyl substituted piperidyl radical, or a lower alkoxy, amino or halo substituted pyridylamino radical, or a carboxamido, mercapto or methylenedioxy substituted anilino radical, or a radical of the formula,

wherein
R is hydrogen or lower alkyl and R' is a nitrogen-containing heterocyclic radical selected from the group consisting of quinuclidinyl, pyrazolyl, 1-triazolyl, isoquinolinyl, indazolyl, benzoxazolyl, thiadiazolyl, and benzothiadiazolyl, and lower alkyl and halo substituted derivatives thereof, or a butyrolactonyl radical, or an adamantyl radical, or a substituted lower alkyl radical selected from the group consisting of mercapto lower alkyl, mono-, di- and tri-lower alkoxy lower alkyl, lower alkyl thio lower alkyl and lower alkoxycarbonyl substituted derivatives thereof, cyano lower alkyl, mono-, di- and tri-lower alkoxy phenyl lower alkyl, phenyl cyclo lower alkyl, 1-pyrrolidinyl lower alkyl, N-lower alkyl pyrrolidinyl lower alkyl, and N-morpholinyl lower alkyl.

Also provided according to the invention are novel methods for treatment of neoplastic disease states in animals, which methods comprise administering a therapeutically effective amount of a compound of the formula, IIa,

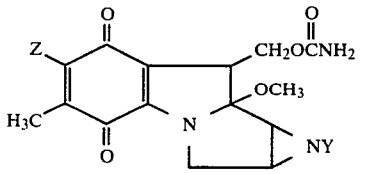

wherein:
Y is hydrogen or lower alkyl; and Z is a lower alkoxy substituted quinolinylamino radical, a cyano substituted pyrazolylamino radical, or a mono- or di- lower alkyl substituted thiazolamino radical, or a nitrogen-containing heterocyclic radical selected from the group consisting of 1-pyrrolinyl, 1-indolinyl, N-thiazolidinyl N-morpholinyl, 1-piperazinyl and N-thiomorpholinyl radicals, or a cyano, phenyl, caraboxamido or lower alkoxycarbonyl substituted 1-aziridinyl radical, or a lower alkyl, formyl or acetylphenyl substituted 1-piperazinyl radical, or an hydroxy or piperidyl substituted piperidyl radical, or a lower alkoxy, amino or halo substituted pyridylamino radical, or a carboxamido, mercapto or methylenedioxy substituted anilino radical, or a radical of the formula,

wherein
R is hydrogen or lower alkyl and R" is a nitrogen-containing heterocyclic radical selected from the group consisting of quinuclidinyl, pyrazolyl, 1-triazolyl, isoquinolinyl, indazolyl, benzoxazolyl, thiadiazolyl and benzothiadiazolyl, and lower alkyl and halo substituted derivatives thereof, or a butyrolactonyl radical, or an adamantyl radical, or a mono-lower alkoxy substituted phenyl radical, or a substituted lower alkyl radical selected from the group consisting of mercapto lower alkyl, carboxy lower alkyl, mono-, di- and tri-lower alkoxy lower alkyl, lower alkyl thio lower alkyl and lower alkoxycarbonyl substituted derivatives thereof, cyano lower alkyl, mono-, di- and tri-lower alkoxy phenyl lower alkyl, phenyl cyclo lower alkyl, 1-pyrrolidinyl lower alkyl, N-lower alkyl pyrrolidinyl lower akyl, N-morpholinyl lower alkyl, and lower dialkylamino lower alkyl.

Unless otherwise indicated, the term "lower", as applied to "alkyl" radicals shall designate such straight or branched chain radicals as include from one to six carbon atoms. By way of illustration, "lower alkyl" shall mean and include methyl, ethyl, propyl, butyl, pentyl and hexyl radicals as well as isopropyl radicals, t-butyl radicals and the like. Similarly, "lower" as applied to "alkoxy" shall designate a radical having one to six carbon atoms.

It will be apparent that the compounds of formula II are all comprehended by the specifications of formula IIa. Put another way, all the novel antibiotic mitomycin derivatives of formula II are useful in practice of the novel antineoplastic therapeutic methods which involve administration of compounds of formula IIa.

Mitomycin derivatives of the invention are prepared by the reaction of mitomycin A with appropriately selected amine compounds. The N-alkylmitomycin (e.g., N-methylmitomycin) derivatives are similarly prepared by the reaction of a selected amine with N-alkylmitomycin A prepared from mitomycin C, e.g., according to the methods generally disclosed in Cheng, et al., *J.Med.Chem.*, 20, No. 6, 767-770 (1977). The preparative reactions generally yield the desired product as a crystalline solid which is readily soluble in alcohol.

Therapeutic methods of the invention comprehend the administration of effective amounts of one or more of the compounds of formula IIa, as an active ingredient, together with desired pharmaceutically acceptable diluents, adjuvants and carriers, to an animal suffering from a neoplastic disease state. Unit dosage forms of compounds administered according to the methods of the invention may range from about 0.001 to about 5.0 mg and preferably from about 0.004 to about 1.0 mg, of the compounds. Such unit dosage quantities may be given to provide a daily dosage of from about 0.1 to about 100 mg per kg., and preferably from about 0.2 to about 51.2 mg per kg, of body weight of the animal treated. Parenteral administration, and especially intraperitoneal administration, is the preferred route for practice of the inventive methods.

Other aspects and advantages of the present invention will become apparent upon consideration of the following description.

DESCRIPTION OF THE INVENTION

The following examples 1 though 42, describing preparation of certain presently preferred compounds according to the invention, are for illustrative purposes only and are not to be construed as limiting the invention. Unless otherwise indicated, all reactions were carried out at room temperature (20° C.), without added heat. Unless otherwise indicated, all thin layer chromatographic (TLC) procedures employed to check the progress of reactions involved the use of a pre-coated silica-gel plate and a mixture of methanol and chloroform (2:8 by volume) as a developing solvent.

EXAMPLE 1

1,1a,2,8,8a,8b-Hexahydro-8-(hydroxymethyl)-8a-methoxy-5-methyl-6-(2-cyano-1-aziridinyl)-azirino[2',3':3,4]pyrrolo[1,2-a]indole-4,7-dione carbamate A solution of mitomycin A (100 mg. or 0.286 mmol) in 8 ml of anhydrous methanol was treated with 2-cyanoaziridine (38.9 mg. or 0.572 mmol) and 30 mg. of potassium carbonate, under nitrogen at room temperature. When thin-layer chromatography on silica gel (2:8 methanol-chloroform as solvent) showed that starting material was no longer present, the mixture was diluted with 50 ml of methylene chloride, filtered, and evaporated under reduced pressure. The residue was purified by preparative thin-layer chromatography on silica gel with a mixture of methanol and chloroform (2:8 by volume) as the solvent. This procedure gave 33 mg. (30% yield) of the desired product having a melting point of 87°–89° C. (decomposing) and providing the following analysis:

NMR (CDCl$_3$, TS): 'δ' values in ppm. The disappearance of a singlet at 4.02 (due to the 6-methoxy group in the starting material) on the appearance of new signals at 2.13 (d, 2) and 2.53 (broad s, 1).

EXAMPLE 2

1,1a,2,8,8a,8b-Hexahydro-8-(hydroxymethyl)-8a-methoxy-5-methyl-6-(thiomorpholinyl)-azirino[2',3':3,4]pyrrolo[1,2-a]indole-4,7-dione carbamate This compound was prepared by the procedure described in Example 1, except that the potassium carbonate was omitted. From 52 mg. of mitomycin A and 500 mg. of thiomorpholine was obtained 14 mg. (22% yield) of the desired product having a melting point of 90°–91° C. (decomposition) and providing the following analysis:

NMR (CDCl$_3$, TS) 'δ' values in ppm. Absence of the 6-methoxy peak at 4.02, and the enhancement of peaks at 2.8 (m, increase by 4) and 3.6 (m, increase by 4).

EXAMPLE 3

1,1a,2,8,8a,8b-Hexahydro-8-(hydroxymethyl)-8a-methoxy-5-methyl-6-(1-indolinyl)-azirino[2',3':3,4]pyrrolo[1,2-a]indole-4,7-dione carbamate This compound was prepared by the procedure described in Example 1, except that the potassium carbonate was omitted. From 100 mg. of mitomycin A and 69 mg. of indoline was obtained 45 mg. (36% yield) of the desired product having a melting point of 127°–135° C. (decomposition) and providing the following analysis:

NMR (CDCl$_3$, TS) 'δ' values in ppm. Absence of the 6-methoxy peak at 4.02, and the appearance of new peaks at 2.85–3.7 (group, 4) and 6.15–7.5 (group, 4).

EXAMPLE 4

1,1a,2,8,8a,8b-Hexahydro-8-(hydroxymethyl)-8a-methoxy-5-methyl-6-[(6-methoxy-3-pyridyl)amino]-azirino[2',3':3,4]-pyrrolo[1,2-a]indole-4,7-dione carbamate This compound was prepared by the procedure described in Example 1, except that the potassium carbonate was omitted. From 100 mg. of mitomycin A and 2 drops of 3-amino-6-methoxypyridine was obtained 96 mg. (76% yield) of the desired product having a melting point of 260°–262° C. (decomposition) and providing the following analysis:

NMR (CDCl$_3$, TS): 'δ' values in ppm. Absence of the 6-methoxy peak at 4.02, and the appearance of new peaks at 3.93 (s, 3), 6.77 (s, 1), 7.26 (d, 1), 7.60 (d, 1) and 7.87 (s, 1).

EXAMPLE 5

1,1a,2,8,8a,8b-Hexahydro-8-(hydroxymethyl)-8a-methoxy-5-methyl-6-[(6-methoxy-8-quinolinyl)amino]-azirino[2',3':3,4]pyrrolo[1,2-a]indole 4,7-dione carbamate This compound was prepared by the procedure described in Example 1. From 60 mg. of mitomycin A and 54 mg. of 8-amino-6-methoxyquinoline was obtained 26 mg. (32% yield) of the desired product having a melting point of 135°–145° C. (decomposition) and providing the following analysis:

NMR (CDCl$_3$, TS) 'δ' values in ppm. Absence of the 6-methoxy peak at 4.02, and the appearance of new peaks at 6.4 (d, 1), 6.67 (d, 1), 7.30 (dd, 1), 8.0 (dd, 1) and 8.90 (dd, 1).

EXAMPLE 6

1,1a,2,8,8a,8b-Hexahydro-8-(hydroxymethyl)-8a-methoxy-5-methyl-6-(3-quinuclidinylamino)-azirino[2',3':3,4]pyrrolo-[1,2-a]indole-4,7-dione carbamate This compound was prepared by the procedure described in Example 1, except that the potassium carbonate was omitted. From 100 mg. of mitomycin A and 3-aminoquinuclidine (prepared by treating an aqueous solution of 73 mg. of 3-aminoquinuclidine hydrochloride with sodium hydroxide) was obtained 86 mg. (54% yield) of the desired product having a melting point of 138°–146° (decomposition) and providing the following analysis:

NMR (CDCl$_3$ TS) 'δ' values in ppm. Absence of the 6-methoxy peak at 4.02 enhancement of the peaks at 2.8 and 3.8, and the appearance of new broad peaks at 1.2 and 2.5.

EXAMPLE 7

1,1a,2,8,8a,8b-Hexahydro-8-(hydroxymethyl)-8a-methoxy-5-methyl-6-[2-(γ-butyrolactonyl)amino]-azirino[2',3':3,4]pyrrolo-1,2-a]indole-4,7-dione carbamate This compound was prepared by the procedure described in Example 1, except that the potassium carbonate was omitted. From 100 mg. of mitomycin A and 60 mg. of α-amino-γ-butyrolactone hydrochloride was obtained 68 mg. (57% yield) of the desired product having a melting point of 87°–89° C. (decomposition) and providing the following analysis:

NMR (DMSO-d$_6$. TS) 'δ' values in ppm. Absence of the 6-methoxy peak at 4.02, and the appearance of new peaks at 1.90–2.87 (m, 2), 3.80–4.70 (m, 3), and 8.3–9.2 (broad s, 1).

EXAMPLE 8

1,1a,2,8,8a,8b-Hexahydro-8-(hydroxymethyl)-8a-methoxy-5-methyl-6-(4-carboxamidoanilino)-azirino[2',3':3,4]pyrrolo-[1,2-a]indole-4,7-dione carbamate This compound was prepared by the procedure described in Example 1. From 100 mg. of mitomycin A and 82 mg. of 4-aminobenzamide was obtained 36 mg. (28% yield) of the desired product having a melting point of 167°–169° C. (decomposition) and providing the following analysis:

NMR (Acetone-d$_6$, TS): 'δ' values in ppm. Absence of the 6-methoxy peak at 4.02, and the appearance of new peaks at 6.67 (d, 3) and 7.73 (d, 2).

EXAMPLE 9

1,1a,2,8,8a,8b-Hexahydro-8-(hydroxymethyl)-8a-methoxy-5-methyl-6-(3,4-dimethoxybenzylamino)-azirino[2',3':3,4]pyrrolo-[1,2-a]indole-4,7-dione carbamate This compound was prepared by the procedure described in Example 1, except that the potassium carbonate was omitted. From 29 mg. of mitomycin A and 69.4 mg. of 3,4-dimethoxybenzylamine was obtained 29 mg. (72% yield) of the desired product having a melting point of 112° C. (decomposition) and providing the following analysis:

NMR (CDCl₃, TS): 'δ' values in ppm. Absence of the 6-methoxy peak at 4.02, and the appearance of new peaks at 3.9 (s, 6), 4.65–4.75 (d, 2), 6.55 (broad s, 1) and 6.86 (s, 3).

EXAMPLE 10

1,1a,2,8,8a,8b-Hexahydro-8-(hydroxymethyl)-8a-methoxy-5-methyl-6-[(1-ethyl-2-pyrrolidino)methylamino]-azirino[2',3':3,4]pyrrolo-[1,2-a]indole-4,-dione carbamate This compound was prepared by the procedure described in Example 1, except that the potassium carbonate was omitted. From 150 mg. of mitomycin A and 2 drops of 2-aminomethyl-1-ethylpyrrolidine was obtained 78 mg. (41% yield) of the desired product decomposing at temperatures above 300° C. and providing the following analysis:

NMR (CDCl₃, TS): 'δ' values in ppm. Absence of the 6-methoxy peak at 4.02, and the appearance of new peaks at 1.07 (t, 3), 1.4–2.33 (m, 5), 2.36–3.03 (m, 4), 3.3–3.83 (m, 2), and 6.77–7.20 (broad S, 1)

EXAMPLE 11

1,1a,2,8,8a,8b-Hexahydro-8-(hydroxymethyl)-8a-methoxy-5-methyl-6-[(1-methoxycarbonyl-3-methylthio)propylamino]-azirino-[2',3':3,4]pyrrolo[1,2-a]indole-4,7-dione carbamate This compound was prepared by the procedure described in Example 1, except that the potassium carbonate was replaced by 0.5 ml. of triethylamine. From 150 mg. of mitomycin A and 110 mg. of L-methionine methyl ester hydrochloride was obtained 64 mg. (30% yield) of the desired product having a melting point of 83°–85° C. (decomposition) and providing the following analysis:

NMR (CDCl₃, TS): 'δ' values in ppm. Absence of the 6-methoxy peak at 4.02, and the appearance of new peaks at 1.63–2.40 (m, 3), 2.10 (s, 3), 2.43–3.0 (m, 2), 3.80 (s, 3) and 8.3, 9.3 (broad s, 1).

EXAMPLE 12

1,1a,2,8,8a,8b-Hexahydro-8-(hydroxymethyl)-8a-methoxy-5-methyl-6-(2-phenylcyclopropylamino)-azirino[2',3':3,4]pyrrolo-[1,2-a]indole-4,7-dione carbamate This compound was prepared by the procedure described in Example 1, except that the potassium carbonate was omitted. From 125 mg. of mitomycin A and 85 mg. of 2-phenylcyclopropylamine was obtained 70 mg. (63%) of the desired product decomposing at temperatures above 250° C. and providing the following analysis:

NMR (CDCl₃, TS): 'δ' values in ppm. Absence of the 6-methoxy peak at 4.02, and the appearance of new peaks at 0.6–1.53 (m, 4), 6.20–6.50 (broad s, 1) and 7.18 (broad s, 5).

EXAMPLE 13

1,1a,2,8,8a,8b-Hexahydro-8-(hydroxymethyl)-8a-methoxy-5-methyl-6-[(5-chloro-2-benzoxazolyl)amino]-azirino[2',3':3,4]pyrrolo[1,2-a]indole-4,7-dione carbamate This compound was prepared by the procedure described in Example 1. From 100 mg. of mitomycin A and 50 mg. of 2-amino-5-chlorobenzoxazole was obtained 35 mg. (25% yield) of the desired product having a melting point of 118°–120° C. (decomposition) and providing the following analysis:

NMR (CDCl₃, TS): 'δ' values in ppm. Absence of the 6-methoxy peak at 4.02, and the appearance of new peaks in the region 6.70–7.63 (m, 4).

EXAMPLE 14

1,1a,2,8,8a,8b-Hexahydro-8-(hydroxymethyl)-8a-methoxy-5-methyl-6-[5-methyl-2-(1,3,4-thiadiazolyl)amino]-azirino-[2',3':3,4]pyrrolo[1,2-a]indole-4,7-dione carbamate This compound was prepared by the procedure described in Example 1. From 100 mg. of mitomycin A and 53 mg. of 2-amino-5-methyl-1,3,4-thiadiazole was obtained 31 mg. (25% yield) of the desired product having a melting point of 91°–93° C. (decomposition) and providing the following analysis:

NMR (CDCl₃, TS): 'δ' values in ppm. Absence of the 6-methoxy peak at 4.02, and the appearance of new peaks at 2.68 (s, 3), and 7.47–7.63 (broad s, 1).

EXAMPLE 15

1,1a,2,8,8a,8b-Hexahydro-8-(hydroxymethyl)-8a-methoxy-5-methyl-6-(2,2-dimethoxyethylamino)-azirino[2',3':3,4]pyrrolo-[1,2-a]indole-4,7-dione carbamate This compound was prepared by the procedure described in Example 1, except that the potassium carbonate was omitted. From 60 mg. of mitomycin A and 35 mg. of 2,2-dimethoxyethylamine was obtained 60 mg. (83% yield) of the desired product decomposing at temperatures above 220° C. and providing the following analysis:

NMR (CDCl₃, TS): 'δ' values in ppm. Absence of the 6-methoxy peak at 4.02, and the appearance of new peaks at 3.45 (s, 6), 3.33–3.93 (m, 2), 4.33–4.85 (broad s, 1) and 6.15–6.66 (broad s, 1.).

EXAMPLE 16

1,1a,2,8,8a,8b-Hexahydro-8-(hydroxymethyl)-8a-methoxy-5-methyl-6-(2-mercaptoethylamino)-azirino[2',3':3,4]pyrrolo-[1,2-a]indole-4,7-dione carbamate This compound was prepared by the procedure described in Example 1, except that 0.5 ml. of triethylamine was used instead of the potassium carbonate. From 150 mg. of mitomycin A and 100 mg. of 2-mercaptoethylamine hydrochloride was obtained 50 mg. (44% yield) of the desired product having a melting point of 152°–154° C. (decomposition) and providing the following analysis:

NMR (DMSO-d₆, TMS): 'δ' values in ppm. Absence of the 6-methoxy peak at 4.02, and the appearance of new peaks at 2.53–3.10 (m, 4), 7.30–7.50 (broad S, 1).

EXAMPLE 17

1,1a,2,8,8a,8b-Hexahydro-8-(hydroxymethyl)-8a-methoxy-5-methyl-6-[(4-methyl-2-thiazolyl)amino]-azirino[2',3':3,4]pyrrolo-[1,2-2]indole-4,7-dione carbamate This compound was prepared by the procedure described in Example 1. From 150 mg. of mitomycin A and 96 mg. of 2-amino-4-methylthiazole was obtained 85 mg. (59% yield) of the desired product having a melting point of 116°–118° C. (decomposition)and providing the following analysis:

NMR (CDCl₃, TS ): 'δ' values in ppm. Absence of the 6-methoxy peak at 4.02, and the appearance of new peaks at 2.23 (s, 3), 6.30–6.60 (broad s, 1) and 7.30 (s, 1).

EXAMPLE 18

1,1a,2,8,8a,8b-Hexahydro-8-(hydroxymethyl)-8a-methoxy-5-methyl-6-(4-mercaptoanilino)-azirino[2',3':3,4]pyrrolo[1,2-a]indole-4,7-dione carbamate This compound was prepared by the procedure described in Example 1, except that the potassium carbonate was omitted. From 200 mg. of mitomycin A and 143 mg. of 4-mercaptoaniline was obtained 120 mg. (47% yield) of the desired product having a melting point of 97°–99° C. (decomposition) and providing the following analysis:

NMR (CDCl₃, TS): 'δ' values in ppm. Absence of the 6-methoxy peak at 4.02, and the appearance of new peaks at 6.53 (d, 2) and 7.0–7.7 (m, 3).

EXAMPLE 19

1,1a,2,8,8a,8b-Hexahydro-8-(hydroxymethyl)-8a-methoxy-5-methyl-6-(3,4-methylenedioxyanilino)-azirino[2',3':3,4]pyrrolo-[1,2-a]indole-4,7-dione carbamate This compound was prepared by the procedure described in Example 1, except that the potassium carbonate was omitted. From 80 mg. of mitomycin A and 0.1 ml. of 3,4-methylenedioxyaniline was obtained 50 mg. (48% yield) of the desired product having a melting point of 86°–88° C. (decomposition) and providing the following analysis:

NMR (CDCl₃, TS): 'δ' values in ppm. Absence of the 6-methoxy peak at 4.02, and the appearance of new peaks at 5.97 (S, 2), 6.0–6.7 (m, 3), 7.27 (S, 1).

EXAMPLE 20

1,1a,2,8,8a,8b-Hexahydro-8-(hydroxymethyl)-8a-methoxy-5-methyl-6-[2-(1-pyrrolidino)ethylamino]-azirino[2',3':3,4]pyrrolo-[1,2-a]indole-4,7-dione carbamate This compound was prepared by the procedure described in Example 1, except that the potassium carbonate was omitted. From 100 mg. of mitomycin A and 0.2 ml. of 2-(1-pyrrolidino) ethylamine was obtained 75 mg. (61% yield) of the desired product decomposing at temperatures above 200° C. and providing the following analysis:

NMR (CDCl₃, TS): 'δ' values in ppm. Absence of the 6-methoxy peak at 4.02, and the appearance of new peaks at 1.57–1.93 (M, 4), 2.33–3.03 (m, 8), and 6.92 (t, 1).

EXAMPLE 21

1,1a,2,8,8a,8b-Hexahydro-8-(hydroxymethyl)-8a-methoxy-5-methyl-6-(5-isoquinolinylamino)-azirino[2',3':3,4]pyrrolo-[1,2-a]indole-4,7-dione carbamate This compound was prepared by the procedure described in Example 1. From 90 mg. of mitomycin A and 810 mg. of 5-aminoisoquinoline was obtained 28 mg. (24% yield) of the desired product having no melting point below 340° C. and providing the following analysis:

NMR (CDCl₃, TS): 'δ' values in ppm. Absence of the 6-methoxy peak at 4.02, and the appearance of new peaks at 6.8–7.65 (m, 3), 7.85 (d, 1) and 8.55 (d, 1).

EXAMPLE 22

1,1a,2,8,8a,8b-Hexahydro-8-(hydroxymethyl)-8a-methoxy-5-methyl-6-(5-indazolylamino)-azirino[2',3':3,4]pyrrolo[1,2-a]indole-4,7-dione carbamate This compound was prepared by the procedure described in Example 1. From 90 mg. of mitomycin A and 666 mg. of 5-aminoindazole was obtained 35 mg. (30% yield) of the desired product having no melting point below 340° C. and providing the following analysis:

NMR (CDCl₃, TS): 'δ' values in ppm. Absence of the 6-methoxy peak at 4.02, and the appearance of new peaks at 6.8–7.65 (m, 3) and 8.0 (S, 1).

EXAMPLE 23

1,1a,2,8,8a,8b-Hexahydro-8-(hydroxymethyl)-8a-methoxy-5-methyl-6-[4-(2,1,3-benzothiadiazolyl)amino]-azirino[2',3':3,4]-pyrrolo[1,2-a]indole-4,7-dione carbamate This compound was prepared by the procedure described in Example 1. The reaction did not go to completion in 19 hours, despite the use of excess amine. From 50 mg. of mitomycin A and 300 mg. of 4-amino-2,1,3-benzothiadiazole was obtained 32 mg. (48%) of the desired product having a melting point of 139°–140° C. (decomposition) and providing the following analysis:

NMR (CDCl₃+CD₃OD, TS): 'δ' values in ppm. Absence of the 6-methoxy peak at 4.02, and the appearance of new peaks at 6.6 (m, 1), 7.6 (m, 2) and 8.25 (broad s, 1).

EXAMPLE 24

1,1a,2,8,8a,8b-Hexahydro-8-(hydroxymethyl)-8a-methoxy-5-methyl-6-(N-glycinyl)-azirino[2',3':3,4]pyrrolo[1,2-a]indole-4,7-dione carbamate This compound was prepared by the procedure described in Example 1, except that 40 ml. of methanol was used and 10 ml. of triethylamine was used instead of potassium carbonate. From 100 mg. of mitomycin A and 600 mg. of glycine was obtained 47.4 mg. (42% yield) of the desired product having no melting point below 350° C. and providing the following analysis:

NMR (CDCl₃+CD₃OD, TS): 'δ' values in ppm. Absence of the 6-methoxy peak at 4.02, and the appearance of a new peak at 3.45 (S, 2).

EXAMPLE 25

1,1a,2,8,8a,8b-Hexahydro-8-(hydroxymethyl)-8a-methoxy-5-methyl-6-(2-cyanoethylamino)-azirino[2',3':3,4]pyrrolo[1,2-a]indole-4,7-dione carbamate This compound was prepared by the procedure described in Example 1, except that 0.5 ml. of triethylamine was used instead of the potassium carbonate. From 210 mg. of mitomycin A and 90 mg. of 3-aminopropionitrile fumanate was obtained 15 mg. (65% yield) of the desired product having a melting point of 68°–70° C. (decomposition) and providing the following analysis:

NMR (CDCl₃, TS): 'δ' values in ppm. Absence of the 6-methoxy peak at 4.02, and the appearance of new peaks at 2.1–2.77 (m, 4) and 6.57 (t, 1).

EXAMPLE 26

1,1a,2,8,8a,8b-Hexahydro-8-(hydroxymethyl)-8a-methoxy-5-methyl-6-(2-fluoroethylamino)-azirino[2',3':3,4]pyrrolo[1,2-a]-indole-4,7-dione carbamate This compound was prepared by the procedure described in Example 1, except that the 2-fluoroethylamine hydrochloride (220 mg.) was neutralized with sodium methoxide (119 mg.) in 2 ml. of methanol at 5° C. before the mitomycin A (77 mg.) was added, and potassium carbonate was not used. A 62 mg. (74%) yield of the desired product was obtained, having no melting point below 340° C. and providing the following analysis:

NMR (CDCl$_3$, TS): 'δ' values in ppm. Absence of the 6-methoxy peak at 4.02, and the appearance of new peaks at 3.3–3.9 (m, 2), 4.2 (t, 2) and 6.5 (broad s, 1).

EXAMPLE 27

1,1a,2,8,8a,8b-Hexahydro-8-(hydroxymethyl)-8a-methoxy-5-methyl-6-[1-(3-pyrrolinyl)]-azirino[2',3':3,4-]pyrrolo[1,2-a]indole-4,7-dione carbamate This compound was prepared by the procedure described in Example 1, except that the potassium carbonate was omitted and a change was made necessary by the presence of pyrrolidine impurity in the commercial sample of 3-pyrroline. The pyrrolidine formed a crystalline derivative with mitomycin A that was removed from the mixture by filtration. The filtrate was then worked up as described in Example 1. From 100 mg. of mitomycin A and 1 g. of commercial 3-pyrroline was obtained 30 mg. (27% yield) of the desired product having a partial decomposition temperature of 85°–90° C., but not melting below 250° C., and providing the following analysis:

NMR (CDCl$_3$, TS): 'δ' values in ppm. Absence of the 6-methoxy peak at 4.02, and the appearance of a new peak at 5.9 (s, 2). It was not possible to distinguish the 2-proton peak in the 3.4 region from other absorption.

EXAMPLE 28

1,1a,2,8,8a,8b-Hexahydro-8-(hydroxymethyl)-8-methoxy-5-methyl-6-(3-thiazolidino)-azirino[2',3':3,4-]pyrrolo[1,2-a]indole-4,7-dione carbamate This compound was prepared by the procedure described in Example 1, except that the potassium carbonate was omitted. From 250 mg. of mitomycin A and 0.5 ml. of thiazolidine was obtained 125 mg. (43% yield) of the desired product having a melting point of 105°–107° C. (decomposition) and providing the following analysis:

NMR CDCl$_3$, TMS): 'δ' values in ppm. Absence of the 6-methoxy peak at 4.02, and the appearance of new peaks at 2.62 (broad S, 2), 2.68–3.02 (broad S, 2), and 3.32–4.02 (broad S, 2).

EXAMPLE 29

1,1a,2,8,8a,8b-Hexahydro-8-(hydroxymethyl)-8a-methoxy-5-methyl-6-[1-(4-methylpiperazino)]-azirino[2',3':3,4]pyrrolo[1,2-a]indole-4,7-dione carbamate This compound was prepared by the procedure described in Example 1, except that the potassium carbonate was omitted. From 100 mg. of mitomycin A and 0.2 ml. of N-methylpiperazine was obtained 50 mg. (42% yield) of the desired product having a melting point of 84°–87° C. (decomposition) and providing the following analysis:

NMR (CDCl$_3$, TS): 'δ' values in ppm. Absence of the 6-methoxy peak at 4.02, and the appearance of new peaks at 2.27 (s, 3), 2.47 (t, 4) and 2.92 (t, 4).

EXAMPLE 30

1,1a,2,8,8a,8b-Hexahydro-8-(hydroxymethyl)-8a-methoxy-5-methyl-6-[3-(pyrazolyl)amino]-azirino[2',3':3,4]pyrrolo[1,2-a]indole-4,7-dione carbamate This compound was prepared by the procedure described in Example 1, except that the potassium carbonate was omitted. From 100 mg. of mitomycin A and 48 mg. of 3-aminopyrazole was obtained 50 mg. (44% yield) of the desired product having a melting point of 142°–145° C. (decomposition) and providing the following analysis:

NMR (CDCl$_3$, TMS): 'δ' values in ppm. Absence of the 6-methoxy peak at 4.02, and the appearance of new peaks at 6.50 (d, 2), 6.67–6.83 (broad S, 1) and 8.07 (S, 1).

EXAMPLE 31

1,1a,2,8,8a,8b-Hexahydro-8-(hydroxymethyl)-8a-methoxy-5-methyl-6-[2-(N-morpholino)ethylamino]-azirino[2',3':3,4]pyrrolo-[1,2-a]indole-4,7-dione carbamate This compound was prepared by the procedure described in Example 1, exept that the potassium carbonate was omitted. From 100 mg. of mitomycin A and 0.5 ml. of N-(2-aminoethyl)morpholine was obtained 70 mg. (55% yield) of the desired product having a melting point of 74°–76° C. (decomposition) and providing the following analysis:

NMR (CDCl$_3$, TS): 'δ' values in ppm. Absence of the 6-methoxy peak at 4.02, and the appearance of new peaks at 2.27–2.73 (broad, 8), 3.47–4.03 (broad, 4) and 7.27 (t, 1).

EXAMPLE 32

1,1a,2,8,8a,8b-Hexahydro-8-(hydroxymethyl)-8a-methoxy-5-methyl-6-[2-(ethylthio)ethylamino]-azirino[2',3':3,4]pyrrolo-[1,2-a-9 indole-4,7-dione carbamate This compound was prepared by the procedure described in Example 1, except that 0.5 ml. of triethylamine was used instead of the potassium carbonate. From 250 mg. of mitomycin A and 101.5 mg. of 2-(ethylthio)ethylamine hydrochloride was obtained 220 mg. (73% yield) of the desired product having a melting point of 103°–106° C. (decomposition) and providing the following analysis:

NMR (CDCl$_3$, TS): 'δ' values in ppm. Absence of the 6-methoxy peak at 4.02, and the appearance of new peaks at 1.27 (t, 3), 2.40–2.90 (m, 4), 3.40–3.93 (m, 2) and 6.56 (t, 1).

EXAMPLE 33

1,1a,2,8,8a,8b-Hexahydro-8-(hydroxymethyl)-8a-methoxy-1,5-dimethyl-6-(2-mercaptoethylamino)-azirino[2',3':3,4]pyrrolo-[1,2-a]indole-4,7-dione carbamate This compound was prepared by the procedure described in Example 1, except that 0.5 ml. of triethylamine was used instead of the potassium carbonate. From 250 mg. of N-methyl-mitomycin A and 78 mg. of 2-mercaptoethylamine hydrochloride was obtained 150 mg. (54% yield) of the desired product having a melting point of 85°–87° C. (decomposition) and providing the following analysis:

NMR (CDCl$_3$, TS): 'δ' values in ppm. Absence of the 6-methoxy group at 4.02, and the appearance of new peaks at 2.57–3.10 (broad s, 4) and 6.20–6.93 (broad s, 1).

EXAMPLE 34

1,1a,2,8,8a,8b-Hexahydro-8-(hydroxymethyl)-8a-methoxy-5-methyl-6-(2-methoxyethylamino)azirino[2',3':3,4]pyrrolo[1,2-a]indole-4,7-dione carbamate This compound was prepared by the procedure described in Example 1, except that the potassium carbonate was omitted. From 120 mg. of mitomycin A and 0.2 ml. of 2-methoxyethylamine was obtained 99 mg. (73% yield) of the desired product having a melting point of 106°–109° C. (decomposition) and providing the following analysis:

NMR CDCl$_3$, TS): 'δ' values in ppm. Absence of the 6-methoxy peak at 4.02, and the appearance of new peaks at 3.42 (S, 3), 3.5–3.9 (broad S, 4), 6.27–6.77 (broad S, 1).

EXAMPLE 35

1,1a,2,8,8a,8b-Hexahydro-8-(hydroxymethyl)-8a-methoxy-5-methyl-6-(4-methoxyanilino)-azirino[2',3':3,4]pyrrolo[1,2-a]indole-4,7-dione carbamate This compound was prepared by the procedure described in Example 1, except that the potassium carbonate was omitted. From 77 mg. of mitomycin A and 27 mg. of 4-methoxyaniline was obtained 70 mg. (74% yield) of the desired product having a melting point of 103°–108° C. (decomposition) and providing the following analysis:

NMR (CDCl$_3$, TS): 'δ' values in ppm. Absence of the 6-methoxy group at 4.02, and the appearance of new peaks at 3.8 (s, 3), 6.8 (s, 4) and 7.7 (s, 1).

EXAMPLE 36

1,1a,2,8,8a,8b-Hexahydro-8-(hydroxymethyl)-8a-methoxy-5-methyl-6-(1-adamantylamino)-azirino[2',3':3,4]pyrrolo[1,2-a]indole-4,7-dione carbamate This compound was prepared by the procedure described in Example 1. The reaction did not go to completion in 48 hours, despite the use of excess amine. From 147 mg. of mitomycin A and 666 mg. of 1-aminoadamantane was obtained 60 mg. (30% yield) of the desired product having melting point of 149°–150° C. (decomposition), with partial decomposition at 85°–90° C., and providing the following analysis:

NMR (CDCl$_3$+CD$_3$OD, TS): 'δ' values in ppm. Absence of the 6-methoxy peak at 4.02, and the appearance of new peaks at 1.55–2.3 (m, 15).

EXAMPLE 37

1,1a,2,8,8a,8b-Hexahydro-8-(hydroxymethyl)8a-methoxy-5-methyl-6-[1-(1,3,4-triazolyl)amino]-azirino[2',3':3,4]pyrrolo[1,2-a]-indole-4,7-dione carbamate This compound was prepared by the procedure described in Example 1. From 100 mg. of mitomycin A and 80 mg. of 1-amino-1,3,4-triazole was obtained 35 mg. (30% yield) of the desired product having a melting point of >250° C. (decomposition) and providing the following analysis:

NMR (CDCl$_3$, TMS): 'δ' values in ppm. Absence of the 6-methoxy peak at 4.02, and the appearance of new peaks at 8.00 (s, 2).

EXAMPLE 38

1,1a,2,8,8a,8b-Hexahydro-8-(hydroxymethyl)-8a-methoxy-5-methyl-6-(3,4,5-trimethoxybenzylamino)-azirino[2',3':3,4]pyrrolo-[1,2-a]indole-4,7-dione carbamate This compound was prepared by the procedure described in Example 1, except that the potassium carbonate was omitted. From 65 mg. of mitomycin A and 437 mg. of 3,4,5-trimethoxybenzylamine was obtained 55 mg. (57% yield) of the desired product having a melting point of 94°–95° C. (decomposition) and providing the following analysis:

NMR (CDCl$_3$, TS): 'δ' values in ppm. Absence of the 6-methoxy peak at 4.02, and the appearance of new peaks at 3.85 (s, 9), 4.46–4.76 (d, 2) and 6.45 (s, 2).

EXAMPLE 39

1,1a,2,8,8a,8b-Hexahydro-8-(hydroxymethyl)-8a-methoxy-1,5-dimethyl-6-[2-(ethylthio)ethylamino]-azirino[2',3':3,4]pyrrolo-[1,2-a]indole-4,7-dione carbamate This compound was prepared by the procedure described in Example 1, except that 0.5 ml. of triethylamine was used instead of the potassium carbonate. From 120 mg. of N-methylmitomycin A and 70 mg. of 2-(ethylthio)ethylamine hydrochloride was obtained 100 mg. (69% yield) of the desired product having a melting point of 114°–116° C. (decomposition) and providing the following analysis:

NMR (CDCl$_3$, TS): 'δ' values in ppm. Absence of the 6-methoxy peak at 4.02, and the appearance of new peaks at 1.27 (t, 3), 2.40–2.93 (m, 4), 3.40–3.93 (m, 2) and 6.50–6.80 (broad s, 1).

EXAMPLE 40

1,1a,2,8,8a,8b-Hexahydro-8-(hydroxymethyl)-8a-methoxy-5-methyl-6-[2-(dimethylamino)ethylamino]-azirino[2',3':3,4]pyrrolo-[1,2-a]indole-4,7-dione carbamate This compound was prepared by the procedure described in Example 1, except that the potassium carbonate was omitted. From 150 mg. of mitomycin A and 0.2 ml. of 2-(dimethylamino)ethylamine was obtained 130 mg. (75% yield) of the desired product having a melting point of 72°–75° C. (decomposition) and providing the following analysis:

NMR (CDCl$_3$, TS): 'δ' values in ppm. Absence of the 6-methoxy peak at 4.02, and the appearance of new peaks at 2.17 (s, 6), 2.37–2.63 (broad s, 2), 3.3–4.0 (broad s, 2) and 6.7–7.1 (broad s, 1).

EXAMPLE 41

1,1a,2,8,8a,8b-Hexahydro-8-(hyroxymethyl)-8a-methoxy-5-methyl-6-[1-(3-hydroxypiperidyl)]-azirino[2',3:3,4]pyrrolo[1,2-a]indole-4,7-dione carbamate This compound was prepared by the procedure described in Example 1, except that 0.5 ml. of triethylamine was used instead of the potassium carbonate. From 130 mg. of mitomycin A and 70 mg. of 3-hydroxypiperidine hydrochloride was obtained 80 mg. (58% yield) of the desired product having a melting point of 98°-101° C. (decomposition) and providing the following analysis:

NMR (CDCl$_3$, TS): 'δ' values in ppm. Absence of the 6-methoxy peak at 4.02, and the appearance of new peaks at 0.97-2.13 (broad m, 4), 2.17-3.13 (broad m, 4), 3.3-4.33 (broad m, 1) and 4.67-5.73 (broad s, 1).

EXAMPLE 42

Through use of mitomycin A and the appropriate amine starting materials, the procedures of the prior examples are susceptible to use in preparation of the following compounds:

(a) 1,1a,2,8,8a,8b-hexahydro-8-(hydroxymethyl)-8a-methoxy-6-(2-phenyl-1-aziridinyl)-azirino[2',3':3,4-]pyrrolo-[1,2-a]indole-4,7-dione carbamate;

(b) 1,1a,2,8,8a,8b-hexahydro-8-(hydroxymethyl)-8a-methoxy-6-(2-methoxycarbonyl-1-aziridinyl)-azirino[2',3':3,4]-pyrrolo-[1,2-a]indole-4,7-dione carbamate;

(c) 1,1a,2,8,8a,8b-hexahydro-8-(hydroxymethyl)-8a-methoxy-6-(2-carboxamido1-aziridinyl)-azirino[2',3':3,4]pyrrolo-[1,2-a]indole-4,7-dione carbamate;

(d) 1,1a,2,8,8a,8b-hexahydro-8-(hydroxymethyl)-8a-methoxy-6-(N-morpholinyl)-azirino[2',3':3,4]pyrrolo-[1,2-a]indole-4,7-dione carbamate;

(e) 1,1a,2,8,8a,8b-hexahydro-8-(hydroxymethyl)-8a-methoxy-6-(1-piperazinyl)-azirino[2',3':3,4]pyrrolo-[1,2-a]indole-4,7-dione carbamate;

(f) 1,1a,2,8,8a,8b-hexahydro-8-(hydroxymethyl)-8a-methoxy-6-(4-formyl-1-piperazinyl)-azirino[2',3':3,4-]pyrrolo-[1,2-a]indole-4,7-dione carbamate;

(g) 1,1a,2,8,8a,8b-hexahydro-8-(hydroxymethyl)-8a-methoxy-6-(4-acetylphenyl-1-piperazinyl)-azirino[2',3':3,4]pyrrolo-[1,2-a]indole-4,7-dione carbamate;

(h) 1,1a,2,8,8a,8b-hexahydro-8-(hydroxymethyl)-8a-methoxy-6-[4-(1-piperidyl)-1-piperidyl]-azirino[2',3':3,4]pyrrolo-[1,2-a]indole-4,7-dione carbamate;

(i) 1,1a,2,8,8a,8b-hexahydro-8-(hydroxymethyl)-8a-methoxy-6-[(6-chloro-3-pyridyl)amino]-azirino[2',3':3,4]pyrrolo-[1,2-a]indole-4,7-dione carbamate;

(j) 1,1a,2,8,8a,8b-hexahydro-8-(hydroxymethyl)-8a-methoxy-6-[(6-amino-3-pyridyl)amino]-azirino[2',3':3,4]pyrrolo-[1,2-a]indole-4,7-dione carbamate;

(k) 1,1a,2,8,8a,8b-hexahydro-8-(hydroxymethyl)-8a-methoxy-6-[(4,5-dimethyl-2-thiazolyl)amino]-azirino[2',3':3,4]pyrrolo-[1,2-a]indole-4,7-dione carbamate;

(l) 1,1a,2,8,8a,8b-hexahydro-8-(hydroxymethyl)-8a-methoxy-6-[(4-cyano-3-pyrazolyl)amino]-azirino[2',3':3,4]pyrrolo-[1,2-a]indole-4,7-dione carbamate.

With specific reference to the compounds comprehended by formula IIa, the above examples illustrate the following structural variations.

1. In the compounds of Examples 33 and 39, Y is lower alkyl and, more specifically, methyl. In all other examples, Y is hydrogen. The identity of Y is independent of the identity of Z. Compare Examples 16 and 33 wherein Z is the same and Y is hydrogen and lower alkyl respectively. See also, Examples 32 and 39 which differ in the same way.

2. Compounds wherein Z is lower alkoxy substituted quinolinylamino radical, a cyano substituted pyrazolamino radical or a mono- or di- lower alkyl substituted thiazolamino radical are represented, respectively, by Examples 5, 42(l), 17, and 42 (k).

3. Compounds wherein Z is a nitrogen-containing heterocyclic radical selected from the group consisting of 1-pyrrolinyl, 1-indolinl, N-thiazolidinyl, N-morpholinyl, 1-piperazinyl and N-thiomorpholinyl radicals are represented, respectively, by Examples 27, 3, 28, 42(d), 42(e), and 2.

4. Compounds wherein Z is a cyano, phenyl, carboxamido or lower alkoxy carbonyl substituted 1-aziridinyl radical are represented, respectively, by Examples 1, 42(a), 42(c) and 42(b).

5. Compounds wherein Z is a lower alkyl, formyl or acetylphenyl substituted 1-piperazinyl radical are represented, respectively, by Examples 29, 42(f) and 42(g).

6. Compounds wherein Z is an hydroxy or piperidyl substituted piperidyl radical are represented, respectively, by Examples 41 and 42(h).

7. Compounds wherein Z is a lower alkoxy, amino or halo substituted pyridylamino radical are represented, respectively, by Examples 4, 42(j) and 42(i).

8. Compounds wherein Z is a carboxamido, mercapto or methylenedioxy substituted anilino radical are represented, respectively, by Examples 8, 18 and 19.

9. Compounds wherein Z is a radial of the formula

and wherein R'' is a nitrogen-containing heterocyclic radical selected from the group consisting of quinuclidinyl, pyrazolyl, 1-triazolyl, isoquinolinyl, indazolyl, benzoxazolyl, thiadiazolyl and benzothiadiazolyl, and lower alkyl and halo substituted derivatives thereof are represented by Examples 6, 30, 37, 21, 22, 13, 14 and 23.

10. Compounds wherein Z is a radical of the formula

and wherein R'' is a butyrolactonyl radical, an adamantyl radical or a mono-lower alkoxy substituted phenyl radical are represented, respectively, by Examples 7, 36 and 35.

11. Compounds wherein Z is a radical of the formula

and R" is a substituted lower alkyl radical selected from the group consisting of mercapto lower alkyl, carboxy lower alkyl, mono-, di- and tri-lower alkoxy lower alkyl, lower alkyl thio lower alkyl and lower alkoxycarbonyl substituted derivatives thereof, cyano lower alkyl, mono-, di- and tri-lower alkoxy phenyl lower alkyl, phenyl cyclo lower alkyl, 1-pyrrolidinyl lower alkyl, N-lower alkyl pyrrolidinyl lower alkyl, N-morpholinyl lower alkyl, and lower dialkylamino lower alkyl are represented by Examples 16, 33, 24, 34, 15, 32, 39, 11, 25, 9, 38, 12, 20, 10, 31 and 40.

Finally, it is noteworthy that use of the compound of Example 26 is comprehended by the disclosure of the use of compounds of the formula Ia in prior application Ser. No. 100,331. It is not encompassed by formula IIa herein.

Compounds according to the present invention, like those of prior application Ser. No. 100,331, are believed to possess anti-bacterial activity against gram-positive and gram-negative microorganisms in a manner similar to that observed for the naturally occurring mitomycins and are thus potentially useful as therapeutic agents in treating bacterial infections in humans and animals.

Usefulness of compounds of formula IIa in the antineoplastic therapeutic methods of the invention is demonstrated by the results of in vivo screening procedures wherein the compounds are administered in varying dosage amounts to mice in which a P338 leukemic condition is induced. The procedures were carried out according to "Lymphocytic Leukemia P338—Protocol 1.200", published in *Cancer Chemotherapy Reports*, Part 3, Vol. 3, No. 2, page 9 (September, 1972). Briefly put, the screening procedures involved administration of the test compound to CDF$^1$ female mice previously infected with $10^6$ ascites cells implanted intraperitoneally. Test compounds were administered on the first day of testing only, and the animals were monitored for vitality, inter alia, over a 35-day period.

Results of screening of compounds of Examples 1 through 41 are set forth in Table I below. Data given includes optimal dose ("OD."), i.e., that dosage in mg/kg of body weight of the animal at which the maximum therapeutic effects are consistently observed. Also included is the median survival time ("MST") expressed as the MST of the test animals compared to the MST of controls $\times 100$ ("% T/C"). Within the context of the in vivo P388 procedure noted above, a % T/C value of 125 or greater indicates significant antineoplastic therapeutic activity. The lowest dose in mg/kg of body weight at which the 125% T/C value is obtained is known as the minimum effective dose ("MED"). These doses also are listed in Table I. It is worthy of note that the exceptionally high MST values obtained in the P388 screenings reported in Table 1 are also indicative of the absence of substantial toxicity of the compounds at the dosages indicated.

TABLE 1

| Example | Optimal Dose mg/kg | MST as % T/C | MED |
|---|---|---|---|
| 1 | 12.8 | 339 | 0.2 |
| 2 | 3.2 | 211 | 0.4 |
| 3 | 12.8 | 150 | 0.8 |
| 4 | 6.4 | 211 | 0.2 |
| 5 | 6.4 | 178 | 0.4 |
| 6 | 25.6 | 144 | 12.8 |
| 7 | 6.4 | 175 | 0.8 |
| 8 | 25.6 | 255 | 1.6 |
| 9 | 25.6 | 239 | 1.6 |
| 10 | 12.8 | 217 | 0.8 |

TABLE 1-continued

| Example | Optimal Dose mg/kg | MST as % T/C | MED |
|---|---|---|---|
| 11 | 6.4 | 131 | 3.2 |
| 12 | 12.8 | 217 | 1.6 |
| 13 | 25.6 | 178 | 1.6 |
| 14 | 12.8 | 222 | 0.8 |
| 15 | 6.4 | 200 | 0.8 |
| 16 | 12.8 | 313 | <0.2 |
| 17 | 6.4 | 172 | 0.4 |
| 18 | 6.4 | 134 | 1.6 |
| 19 | 3.2 | 167 | <0.2 |
| 20 | 12.8 | 194 | 0.4 |
| 21 | 12.8 | 183 | 0.2 |
| 22 | 25.6 | 206 | 0.2 |
| 23 | 12.8 | 161 | 0.8 |
| 24 | 6.4 | 261 | 0.4 |
| 25 | 6.4 | 232 | 0.4 |
| 26 | 6.4 | >316 | 0.4 |
| 27 | 12.8 | 216 | 0.2 |
| 28 | 25.6 | 222 | 0.2 |
| 29 | 3.2 | 261 | <0.2 |
| 30 | 25.6 | >333 | 0.8 |
| 31 | 25.6 | 150 | 6.4 |
| 32 | 12.8 | 205 | 1.6 |
| 33 | 25.6 | 170 | 1.6 |
| 34 | 12.8 | 205 | 0.8 |
| 35 | 12.8 | >316 | 0.8 |
| 36 | 25.6 | 132 | 6.4 |
| 37 | 12.8 | 172 | 3.2 |
| 38 | 25.6 | 188 | 1.6 |
| 39 | 25.6 | 200 | 6.4 |
| 40 | 12.8 | >211 | 0.4 |
| 41 | 12.8 | >211 | <0.2 |

Clearly among the most preferred compounds employed as antineoplastic agents according to the invention are those exhibiting more than twice the relative life-extending capacity generally characterized as evidencing significant therapeutic potential, i.e., those having an MST % T/C value greater than $2 \times 125$. The class of such compounds is seen to include the compounds of Examples 1, 8, 16, 24, 26, 29, 30 and 35.

As may be noted from Table I, initial single dosages of as little as 0.2 mg/kg showed substantial long term antineoplastic activity. Accordingly, the methods of the invention may involve therapeutic administration of unit dosages of as little as 0.001 mg or as much as 5 mg, preferably from 0.004 mg to 1.0 mg, of the compounds as the active ingredient in a suitable pharmaceutical preparation. Such preparations may be administered in a daily regimen calling for from 0.1 mg to 100 mg per kg, preferably from about 0.2 to about 51.2 mg per kg, of the body weight of the animal suffering from neoplastic disease. It is preferred that the compounds be administered parenterally. Pharmaceutical compositions suitable for use in practice of methods of the invention may comprise simple water solutions of one or more of the compounds of formula IIa, but may also include well known pharmaceutically acceptable diluents adjuvants and/or carriers such as saline suitable for medicinal use.

Further aspects and advantages of the present invention are expected to occur to those skilled in the art upon consideration of the foregoing description and consequently only such limitations as appear in the appended claims should be placed thereon.

What is claimed is:

1. A compound of the formula,

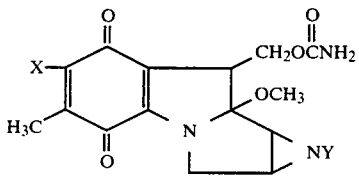

wherein Y is hydrogen or lower alkyl and X is a carboxamido or mercapto or methylenedioxy substituted anilino.

2. A compound according to claim 1 named:

1,1a,2,8,8a,8b-hexahydro-8-(hydroxymethyl)-8a-methoxy-5-methyl-6-(4-carboxyamidoanilino)-azirino[2',3':3,4]pyrrolo-[1,2-a]-indole-4, 7-dione carbamate;

1,1a,2,8,8a,8b-hexahydro-8-(hydroxymethyl)-8a-methoxy-5-methyl-6-(4-mercaptoanilino)-azirino[2',3':3,4]pyrrolo-[1,2-a]-indole-4,7-dione carbamate; or 1,1a,2,8,8a,8b-hexahydro-8-(hydroxymethyl)-8a-methoxy-5-methyl-6-(3, 4-methylenedioxyanilino)-azirino[2',3':3,4]pyrrolo[1,2-a]-indole-4,7-dione carbamate.

3. A compound of the formula,

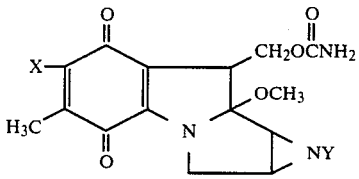

wherein Y is hydrogen or lower alkyl and X is a radical of the formula,

wherein R is hydrogen or lower alkyl and R' is a substituted lower alkyl radical selected from the group consisting of mercapto lower alkyl, mono-, di- and tri-lower alkoxy lower alkyl, lower alkyl thio lower alkyl, and lower alkoxycarbonyl substituted derivatives thereof, cyano lower alkyl, mono-, di-, and tri-lower alkoxy phenyl lower alkyl, pyrrolidinyl lower alkyl, or lower alkyl substituted derivatives thereof, and morpholinyl lower alkyl.

4. A compound according to claim 3 named:

1,1a,2,8,8a,8b-hexahydro-8-(hydroxymethyl)-8a-methoxy-5-methyl-6-(2-mercaptoethylamino)-azirino[2',3':3,4]pyrrolo-[1,2-a]-indole-4,7-dione carbamate;

1,1a,2,8,8a,8b-hexahydro-8-(hydroxymethyl)-8a-methoxyl-1,5-dimethyl-6-(2-mercaptoethylamino)-azirino[2',3':3,4]pyrrolo-[1,2-a]-indole-4,7-dione carbamate;

1,1a, 2,8,8a,8b-hexahydro-8-(hydroxymethyl)-8a-methoxy-5-methyl-6-(2,2-dimethoxyethylamino)-azirino[2',3':3,4]pyrrolo-[1,2-a]-indole-4,7-dione carbamate;

1,1a,2,8,8a,8b-hexahydro-8-(hydroxymethyl)-8a-methoxy-5-methyl-6-(methoxyethylamino)-azirino[2',3':3,4]pyrrolo-[1,2-a]-indole-4,7-dione carbamate;

1,1a,2,8,8a,8b-hexahydro-8-(hydroxymethyl)-8a-methoxy-5-methyl-6-[2-(ethylthio)ethylamino]-azirino[2',3':3,4]pyrrolo-[1,2-a]-indole-4,7-dione carbamate;

1,1a,2,8,8a,8b-hexahydro-8-(hydroxymethyl)-8a-methoxy-1,5-dimethyl-6-[(2-(ethylthio) ethylamino]-azirino[2',3';3,4]pyrrolo-[1,2-a]-indole-4,7-dione carbamate;

1,1a,2,8,8a,8b-hexahydro-8-(hydroxymethyl)-8a-methoxy-5-methyl-6-[(1-methoxycarbonyl-3-methylthio)propylaminoazirino[1,2-a]pyrrolo-[1,2-a]-indole-4,7-dione carbamate;

1,1a,2,8,8a,8b-hexahydro-8-(hydroxymethyl)-8a-methoxy-5-methyl-6-(2-cyanoethylamino)-azirino[2',3':3,4] pyrrolo[1,2]-indole-4,7-dione carbamate;

1,1a,2,8,8a,8b-hexahydro-8-(hydroxymethyl)8a-methoxy-5-methyl-6-(3, 4-dimethoxybenzylamino)-azirino[2',3':3,4] pyrrolo[1,2a]-indole-4,7-dione carbamate;

1,1a,2,8,8a,8b-hexahydro-8-(hydroxymethyl)-8a-methoxy-5-methyl-6-(3,4,5-trimethoxybenzylamino)-azirino[2',3':3,4]pyrrolo-[1,2-a]-indole-4, 7-dione carbamate;

1,1a,2,8,8a,8b-hexahydro-8-(hydroxymethyl)-8a-methoxy-5-methyl-6-[2-(1-pyrrolidino)ethylamino]-azirino[2',3':3,4]pyrrolo-[1,2-a]-indole-4,7-dione carbamate;

1,1a,2,8,8a,8b-hexahydro-8-(hydroxymethyl)-8a-methoxy-5-methyl-6-[(1-ethyl-2-pyrrolidino)methylamino]-azirino [2',3':3,4] pyrrolo-[1,2-a]-indole-4,7-dione carbamate; or 1,1a,2,8,8a,8b-hexahydro-8-(hydroxymethyl)-8a-methoxy-5-methyl-6-[2-(N-morpholino)ethylamino]-azirino[2',3':3,4]pyrrolo-[1,2a]-indole-4,7-dione carbamate.

5. A compound of the formula,

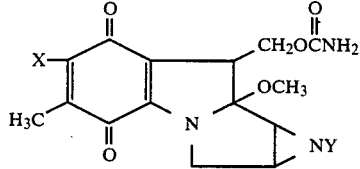

wherein Y is hydrogen or lower alkyl and X is a nitrogen containing heterocyclic radical selected from the group consisting of formyl or acetylphenyl substituted 1-piperazinyl and lower alkoxy or amino substituted pyridyl amino.

6. A compound according to claim 5 named:

1,1a,2,8,8a,8b-hexahydro-8-(hydroxymethyl)-8a-methoxy-5-methyl-6-(4-formyl-1-piperazinyl)-azirino[2',3':3,4] pyrrolo[1,2-A]-indole-4,7-dione carbamate;

1,1a,2,8,8a,8b-hexahydro-8-(hydroxymethyl)-8a-methoxy-5-methyl-6-(4-acetylphenyl-1-piperazinyl)-azirino[2',3':3,4]pyrrolo-[1,2-a]-indole-4,7-dione carbamate;

1,1a,2,8,8a,8b-hexahydro-8-(hydroxymethyl)-8a-methoxy-5-methyl-6-[(6-methoxy-3-pyridyl)amino]-azirino[2',3':3,4]pyrrolo-[1,2-a]-indole-4,7-dione carbamate;

1,1a,2,8,8a,8b-hexahydro-8-(hydroxymethyl)-8a-methoxy-5-methyl-6-[(6-amino-3-pyridyl)amino]- azirino[2',3':3,4] pyrrolo[1,2-a]-indole-4,7-dione carbamate.

7. A compound of the formula,

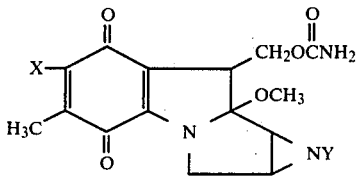

wherein Y is hydrogen or lower alkyl and X is a nitrogen-containing heterocyclic radical selected from the group consisting of cyano or phenyl or lower alkoxy carbonyl or carboxamido substituted 1-aziridinyl, N-triazolodinyl, 1-indolinyl, 1-pyrrolinyl, and hydroxy or piperidyl substituted piperidyl.

8. A compound according to claim 7 named:
1,1a,2,8,8a,8b-hexahydro-8-(hydroxymethyl)-8a-methoxy-5-methyl-6-(2-cyano-1-aziridinyl)-azirino[2',3':3,4] pyrrolo[1,2-a]-indole-4,7-dione carbamate;
1,1a,2,8,8a,8b-hexahydro-8-(hydroxymethyl)-8a-methoxy-5-methyl-6-(2phenyl-1-aziridinyl)-azirino[2',3':3,4] pyrrolo[1,2-a]-indole-4,7-dione carmate;
1,1a,2,8,8a,8b-hexahydro-8-(hydroxymethyl)-8a-methoxy-5-methyl-6-(2-methoxycarbonyl-1-aziridinyl)-azirino[2',3':3,4]pyrrolo-[1,2-a]-indole-4,7-dione carbamate;
1,1a,2,8,8a,8b-hexahydro-8-(hydroxymethyl)-8a-methoxy-5-methyl-6-(2-carboxamido-1-aziridinyl)-azirino[2',3':3,4]pyrrolo-[1,2-a]-indole-4,7-dione carbamate;
1,1a,2,8,8a,8b-hexahydro-8-(hydroxymethyl)-8a-methoxy-5-methyl-6-(1-indolinyl)-azirino[2',3':3,4] pyrrolo-[1,2-a]-indole-4,7-dione carbamate;
1,1a,2,8,8a,8b-hexahydro-8-(hydroxymethyl)-8a-methoxy-5-methyl-6-[1(3pyrrolinyl)]-azirino[2',3':3,4] pyrrolo-[1,2-a]indole-4,7-dione carbamate;
1,1a,2,8,8a,8b-hexahydro-8-(hydroxymethyl)-8a-methoxy-5-methyl-6-(3-thiazolidino)-azirino[2',3':3,4] pyrrolo-[1,2-a]indole-4,7-dione carbamate;
1,1a,2,8,8a,8b-hexahydro-8-(hydroxymethyl)-8a-methoxy-5-methyl-6-[4-(1-piperidyl)-1-piperidyl)-azirino[2',3':3,4]pyrrolo-[1,2-a]-indole-4,7-dione carbamate; or
1,1a,2,8,8a,8b-hexahydro-8-(hydroxymethyl)-8a-methoxy-5-methyl-6-[1-[3-hydroxypiperidyl)]-azirino[2',3':3,4] pyrrolo[1,2-a]-indole-4,7-dione carbamate.

9. A compound of the formula,

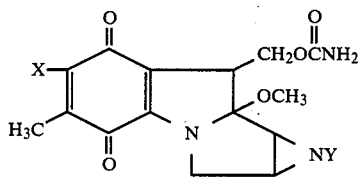

wherein Y is hydrogen or lower alkyl and X is a radical of the formula,

wherein R is hydrogen or lower alkyl and R' is
a heterocyclic radical selected from the group consisting of quinuclidinyl, benzoxazolyl or a halo substituted derivative thereof, thiadiazolyl or a lower alkyl substituted derivative thereof, thiazolyl or a mono- or di-lower alkyl substituted derivative thereof, indazolyl, benzothiadiazolyl, pyrazolyl or a cyano substituted derivative thereof, 1-triazolyl and butyrolactonyl or
an adamantyl radical.

10. A compound according to claim 9 named:
1,1a,2,8,8a,8b-hexahydro-8-(hydroxymethyl)-8a-methoxy-5-methyl-6-(3-quinuclidinylamino)-azirino[2',3':3,4]pyrrolo[1,2a]-indole-4,7-dione carbamate;
1,1a,2,8,8a,8b-hexahydro-8-(hydroxymethyl)-8a-methoxy-5-methyl-6-[(5-chloro-2-benzoxazolyl)amino]-azirino[2',3':3,4]pyrrolo-[1,2-a]-indole-4,7-dione carbamate;
1,1a,2,8,8a,8b-hexahydro-8-(hydroxymethyl)-8a-methoxy-5-methyl-6-[5methyl-2-(1,3,4-thiadiazolyl)amino]-azirino [2',3':3,4] pyrrolo[1,2-a]-indole-4,7-dione carbamate;
1,1a,2,8,8a,8b-hexahydro-8-(hydroxymethyl)-8a-methoxy-5-methyl-6-[(4-methyl-2-thiazolyl)amino]-azirino[2',3':3,4] pyrrolo[1,2-a]-indole-4,7-dione carbamate;
1,1a,2,8,8a,8b-hexahydro-8-(hydroxymethyl)-8a-methoxy-5-methyl-6-[(4,5-dimethyl-2-thiazolyl)amino]-azirino[2',3':3,4]pyrrolo-[1,2-a]-indole-4,7-dione carbamate;
1,1a,2,8,8a,8b-hexahydro-8-(hydroxymethyl)-8a-methoxy-5-methyl-6-(5-indazolylamino)-azirino[2',3':3,4]pyrrolo[1,2-a]indole-4,7-dione carbamate;
1,1a,2,8,8a,8b-hexahydro-8-(hydroxymethyl)-8a-methoxy-5-methyl-6-[4-(2,1,3-benzothiadiazolyl)amino]-azirino[2',3':3,4]pyrrolo-[1,2-a]-indole-4,7-dione carbamate;
1,1a,2,8,8a,8b-hexahydro-8-(hydroxymethyl)-8a-methoxy-5-methyl-6-[3-(pyrazolyl)amino]-azirino[2',3':3,4] pyrrolo[1,2-a]-indole-4,7-dione carbamate;
1,1a,2,8,8a,8b-hexahydro-8-(hydroxymethyl)-8a-methoxy-5-methyl-6-[(4-cyano-3-pyrazolyl)amino]-azirino[2',3':3,4]pyrrolo-[1,2-a]-indole-4,7-dione carbamate;
1,1a,2,8,8a,8b-hexahydro-8-(hydroxymethyl)-8a-methoxy-5-methyl-6-[1-(1,3,4-triazolyl)amino]-azirino[2',3':3,4]pyrrolo[1,2-a]-indole-4,7-dione carbamate;
1,1a,2,8,8a,8b-hexahydro-8-(hydroxymethyl)-8a-methoxy-5-methyl-6-[2-(-butyrolactonyl)amino]-azirino[2',3':3,4]pyrrolo[1,2-a]-indole-4,7-dione carbamate; or
1,1a,2,8,8a,8b-hexahydro-8-(hydroxymethyl)-8a-methoxy-5-methyl-6-(1-adamantylamino)-azirino[2',3':3,4]pyrrolo-[1,2-a]indole-4,7-dione carbamate.

* * * * *

UNITED STATES PATENT AND TRADEMARK OFFICE
CERTIFICATE OF CORRECTION

PATENT NO. : 4,617,389

DATED : October 14, 1986

INVENTOR(S) : WILLIAM A. REMERS

It is certified that error appears in the above-identified patent and that said Letters Patent is hereby corrected as shown below:

Column 3, line 24, change "caraboxamido" to "carboxamido";
Column 6, line 46, insert a carriage return after "carbamate" which should be centered;
Column 6, line 51, line should not be centered;

Column 7, line 10, insert a carriage return after "carbamate";
Column 7, lines 13, 16 and 17, lines should not be centered;

Column 8, line 10, move ")" to end of line 9;
Column 8, line 56, change "broad S" from bold print to regular print;
Column 9, line 54, change "m" from bold print to regular print;
Column 10, line 22, move ")" to end of line 21;
Column 16, line 20, change "1-indolinl" to "1-indolinyl";
Column 19, line 23 and Column 20, line 18, change "(3,   4-methylenedioxy-anilino)" to "(3,4-methylenedioxyanilino)";
Column 21, line 28, change "mate" to "bamate";
Column 21, line 49, change "1,1a,2,8,8a,8b-   hexahydro" to "1,1a,2,8,8a,8b-hexahydro".

Signed and Sealed this

Third Day of February, 1987

Attest:

DONALD J. QUIGG

Attesting Officer

Commissioner of Patents and Trademarks